(12) United States Patent
Nojiri et al.

(10) Patent No.: US 9,493,762 B2
(45) Date of Patent: Nov. 15, 2016

(54) VECTOR, A TRANSFORMANT AND A METHOD TO PRODUCE A POLYPEPTIDE HAVING ACTIVITY TO SELECTIVELY HYDROLYZE A (R)-TROPIC ACID AMIDE IN A RACEMIC MIXTURE

(71) Applicant: KANEKA CORPORATION, Osaka-shi, Osaka (JP)

(72) Inventors: Masutoshi Nojiri, Takasago (JP); Hiroyuki Kanamaru, Takasago (JP); Akiko Nishi, Takasago (JP); Shigeru Kawano, Takasago (JP); Yoshihiko Yasohara, Takasago (JP)

(73) Assignee: KANEKA CORPORATION, Osaka-Shi, Osaka (JP)

( * ) Notice: Subject to any disclaimer, the term of this patent is extended or adjusted under 35 U.S.C. 154(b) by 238 days.

(21) Appl. No.: 14/348,528

(22) PCT Filed: Sep. 28, 2012

(86) PCT No.: PCT/JP2012/075123
§ 371 (c)(1),
(2) Date: Mar. 28, 2014

(87) PCT Pub. No.: WO2013/047767
PCT Pub. Date: Apr. 4, 2013

(65) Prior Publication Data
US 2014/0335575 A1    Nov. 13, 2014

(30) Foreign Application Priority Data
Sep. 29, 2011 (JP) ................. 2011-214381

(51) Int. Cl.
| | |
|---|---|
| *C12N 9/80* | (2006.01) |
| *C12N 15/00* | (2006.01) |
| *C12N 5/10* | (2006.01) |
| *C12N 1/21* | (2006.01) |
| *C12P 13/02* | (2006.01) |
| *C12P 7/40* | (2006.01) |
| *C12P 41/00* | (2006.01) |
| *C12P 7/42* | (2006.01) |
| *C12P 13/04* | (2006.01) |

(52) U.S. Cl.
CPC . *C12N 9/80* (2013.01); *C12P 7/40* (2013.01); *C12P 7/42* (2013.01); *C12P 13/02* (2013.01); *C12P 13/04* (2013.01); *C12P 41/006* (2013.01); *Y02P 20/52* (2015.11)

(58) Field of Classification Search
CPC .......... C12N 9/80; C12P 13/02; C12P 13/04; C12P 41/006; C12P 7/40; C12P 7/42; Y02P 20/52
See application file for complete search history.

(56) References Cited

U.S. PATENT DOCUMENTS 6,063,615 A    5/2000 Sturmer et al.
2012/0040418 A1    2/2012 Araki et al.

FOREIGN PATENT DOCUMENTS

| CN | 1203949 A | 1/1999 |
| JP | 2007-29017 A | 2/2007 |
| WO | WO 97/12964 A2 | 4/1997 |
| WO | WO 97/12964 A3 | 4/1997 |
| WO | WO 2010/125829 A1 | 11/2010 |

OTHER PUBLICATIONS

Nishiyama et al., GenBank accession No. P27765, Aug. 10, 2010.*
Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Brown et al., GenBank accession No. EJM41240, 2012.*
Sadowski et al., Current Opinion in Structural Biology 19:357-362, 2009.*
Extended European Search Report issued in European Patent Application No. 12835997.3 on Mar. 23, 2015.
Nishiyama et al., "Cloning and Characterization of Genes Responsible for Metabolism of Nitrile Compounds from Pseudomonas chlororaphis B23", Journal of Bacteriology, vol. 173, No. 8 (1991) pp. 2465-2472.
International Search Report, issued in PCT/JP2012/075123, dated, Oct. 23, 2012.
Klomp et al., Enzymatic kinetic resolution of tropic acid, Tetrahedron:Asymmetry, 2005, vol. 16, Issue 23, pp. 3892-3896.
Wang et al., Enzymatic hydrolytic resolution of (R,S)-tropic acid esters and (R,S)-ethyl • -methoxyphenyl acetate in biphasic media, Journal of Molecular Catalysis B: Enzymatic, 2009, vol. 57, Issue 1-4, pp. 158-163.

* cited by examiner

*Primary Examiner* — Delia Ramirez
(74) *Attorney, Agent, or Firm* — Birch, Stewart, Kolasch & Birch, LLP

(57) ABSTRACT

An object of the present invention is to provide a means for producing an optically active tropic acid that is a compound useful as a synthetic raw material or an intermediate for pharmaceutical products and the like. The present invention provides a novel polypeptide having activity to (R)-selectively hydrolyze a racemic tropic acid amide, DNA encoding the polypeptide, a vector containing the DNA, a transformant prepared by transformation with the vector, and a method for producing an optically active carboxylic acid amide and an optically active carboxylic acid using them.

6 Claims, No Drawings

SEQUENCE LISTING

<160> NUMBER OF SEQ ID NOS: 16

<210> SEQ ID NO 1
<211> LENGTH: 504
<212> TYPE: PRT
<213> ORGANISM: Artificial Sequence
<220> FEATURE:
<223> OTHER INFORMATION: Isolated from strain KNK AM38

<400> SEQUENCE: 1

Met Ala Ile Val Arg Pro Thr Leu Asp Gln Leu Gln Asp Ile Ala Gly
1               5                   10                  15

Arg Leu Asn Met Gln Leu Thr His Glu Gln Ala Ala Glu Tyr Leu Ala
            20                  25                  30

Leu Met Gln Pro Ser Phe Asp Ala Tyr Asp Leu Val Asp Glu Leu Pro
        35                  40                  45

Asp Phe Thr Pro Pro Val Arg Tyr Asp Arg Ser Ser Gly Tyr Arg Pro
    50                  55                  60

Ser Asn Pro Gln Asn Leu Leu Asn Ala Trp Tyr Tyr Arg Thr Glu Val
65                  70                  75                  80

```
Asn Gly Ala Arg Glu Gly Lys Leu Ala Gly Lys Thr Val Ala Leu Lys
             85                  90                  95

Asp Asn Ile Ser Leu Ala Gly Val Pro Met Met Asn Gly Ala Thr Pro
            100                 105                 110

Leu Glu Gly Phe Val Pro Lys Phe Asp Ala Thr Val Val Thr Arg Leu
            115                 120                 125

Leu Asp Ala Gly Ala Thr Ile Leu Gly Lys Ala Thr Cys Glu His Tyr
            130                 135                 140

Cys Leu Ser Gly Gly Ser His Thr Ser Asp Pro Ala Pro Val His Asn
145                 150                 155                 160

Pro Tyr Arg His Gly Phe Ala Gly Gly Ser Ser Ser Gly Ser Ala
                165                 170                 175

Ala Leu Val Ala Ala Gly Glu Val Asp Leu Ala Val Gly Gly Asp Gln
            180                 185                 190

Gly Gly Ser Ile Arg Ile Pro Ser Ala Phe Cys Gly Thr Tyr Gly Met
            195                 200                 205

Lys Pro Thr His Gly Leu Val Pro Tyr Thr Gly Ile Met Ala Ile Glu
            210                 215                 220

Ala Thr Ile Asp His Ala Gly Pro Ile Thr Arg Asn Val Arg Asp Asn
225                 230                 235                 240

Ala Leu Met Leu Glu Val Met Ala Gly Ala Asp Gly Leu Asp Pro Arg
                245                 250                 255

Gln Ala Ala Pro Gln Val Asp Ala Tyr Cys Asp Tyr Leu Glu Arg Gly
            260                 265                 270

Val Ser Gly Leu Arg Ile Gly Ile Leu Gln Glu Gly Phe Gln Leu Ala
            275                 280                 285

Asn Gln Asp Pro Arg Val Ala Asp Lys Val Arg Ser Ala Ile Ala Arg
            290                 295                 300

Leu Glu Val Leu Gly Ala Arg Val Glu Glu Val Ser Val Pro Glu His
305                 310                 315                 320

Asn Leu Ala Gly Ser Leu Trp His Pro Ile Gly Cys Glu Gly Leu Thr
                325                 330                 335

Met Gln Met Met His Gly Asn Gly Ala Gly Phe Asn Trp Lys Gly Leu
            340                 345                 350

Tyr Asp Val Gly Leu Leu Asp Lys Gln Ala Gly Trp Arg Glu Gln Ala
            355                 360                 365

Asn Ala Leu Ser Ala Ser Leu Lys Leu Cys Met Phe Val Gly Gln Tyr
            370                 375                 380

Gly Leu Glu Arg Tyr Asn Gly Arg Phe Tyr Ala Lys Ala Gln Asn Ile
385                 390                 395                 400

Ala Arg Phe Ala Arg Ala Gly Tyr Asp Lys Ala Leu Gln Thr Tyr Asp
            405                 410                 415

Leu Leu Val Met Pro Thr Val Pro Ile Ile Ala Gln Pro His Pro Glu
            420                 425                 430

Pro Asp Cys Ser Ile Thr Asp Tyr Val Ala Arg Ala Leu Glu Met Ile
            435                 440                 445

Gly Asn Thr Ala Pro Gln Asp Ile Thr Gly His Pro Ala Met Ser Ile
            450                 455                 460

Pro Cys Gly Leu Val Asp Gly Leu Pro Leu Gly Leu Met Phe Val Gly
465                 470                 475                 480

Lys His Tyr Ala Glu Gly Thr Ile Tyr Gln Ala Ala Ala Ala Phe Glu
                485                 490                 495

Ala Ala Val Asp Trp Lys Thr Leu
```

<210> SEQ ID NO 2
<211> LENGTH: 1515
<212> TYPE: DNA
<213> ORGANISM: Artificial Sequence
<220> FEATURE:
<223> OTHER INFORMATION: Isolated from strain KNK AM38

<400> SEQUENCE: 2

```
atggccattg ttcgccctac cctcgaccaa ctgcaggaca tcgctggccg gctgaatatg      60
cagctgactc acgagcaggc agcggaatac ctggcactca tgcagccaag tttcgacgca     120
tatgacctgg tcgacgagtt gccggatttc accccgccgg tgcgctacga ccgcagttcg     180
ggctaccgcc cgtcaaaccc gcaaaaacctg ctcaatgcct ggtattacag gactgaggtg     240
aatggcgccc gtgagggcaa acttgctggc aagactgttg ccctcaagga caacatctcc     300
ctggctgggg ttccgatgat gaacggggcc accccactgg aaggcttcgt accgaaattc     360
gacgctaccg tggtcacccg gttgctagac gccgggcta ccatcctggg caaggcgacc     420
tgtgagcact actgcctctc cggtggcagc catacgtctg atccggcgcc cgtacacaac     480
ccataccggc acgttttcgc cgccggcgga tcctcctccg aagcgctgc gttggtagca     540
gccggcgagg tggacctggc ggttggcggc gatcaaggcg gctcgatccg catcccttca     600
gcgttctgcg gcacctatgg catgaagccg acccacggcc tggtgcctta caccggcatc     660
atggcgatcg aagccacgat cgaccatgcc ggtcccatca cccgcaacgt gcgtgacaac     720
gcgctgatgc tggaagtcat ggccggtgcc gacggactcg accctcgcca ggccgcgcct     780
caggtcgacg cctactgcga ctatctggag cgaggtgtga gcgggctgcg gatcggcatc     840
ctgcaggaag gtttccaact ggccaatcag gatccgcgtg ttgccgacaa ggtgcgcagc     900
gccatcgccc gacttgaggt cttgggcgct cgcgtcgagg aagtctccgt ccccgagcac     960
aacctggcgg ttcgctgtg caccccatc ggctgcgaag gcctgaccat gcagatgatg    1020
catggcaacg gcgcaggctt taactggaag gggctctacg acgtcggcct gctggataaa    1080
caggccggct ggcgcgaaca gcgaacgca ttgtccgcgt cgctcaagct gtgcatgttc    1140
gtcggccaat acggcctgga acgttacaac ggtcgcttct acgccaaggc tcagaacatc    1200
gcacgcttcg ctcgggccgg ttacgacaag gcactgcaaa cctatgacct tctggtcatg    1260
ccgaccgtgc cgatcattgc ccagcctcac cccgaacccg attgttcgat caccgattac    1320
gtggcccgtg cactggaaat gatcggcaac accgcgccgc aggacattac cggccatccg    1380
gccatgtcga tcccgtgtgg tctggtggac ggcctgccct tggggctgat gttcgttggc    1440
aagcactatg ccgaaggcac gatttaccag gcggcggcag cgttcgaggc cgctgtcgac    1500
tggaagacgt tgtaa                                                     1515
```

<210> SEQ ID NO 3
<211> LENGTH: 504
<212> TYPE: PRT
<213> ORGANISM: Artificial Sequence
<220> FEATURE:
<223> OTHER INFORMATION: Isolated from strain KNK AM40

<400> SEQUENCE: 3

```
Met Ala Ile Val Arg Pro Thr Leu Asp Gln Leu Gln Asp Ile Ala Gly
1               5                   10                  15

Gln Leu Asn Met Gln Leu Thr His Glu Gln Ala Val Glu Tyr Leu Ala
            20                  25                  30
```

```
Leu Met Gln Pro Ser Phe Asp Ala Tyr Asp Leu Val Asp Glu Leu Pro
            35                  40                  45

Asp Phe Thr Pro Ser Val Arg Tyr Asp Arg Ser Ser Gly Tyr Arg Pro
 50                  55                  60

Ser Asn Pro Gln Asn Leu Leu Asn Ala Trp Tyr Tyr Arg Thr Glu Val
 65                  70                  75                  80

Asn Gly Ala Arg Glu Gly Lys Leu Ala Gly Lys Thr Val Ala Leu Lys
                 85                  90                  95

Asp Asn Ile Ala Leu Ala Gly Val Pro Met Met Asn Gly Ala Ser Ile
                100                 105                 110

Leu Glu Gly Phe Val Pro Ser Phe Asp Ala Thr Val Val Thr Arg Leu
            115                 120                 125

Leu Asp Ala Gly Ala Thr Ile Leu Gly Lys Ala Thr Cys Glu His Tyr
            130                 135                 140

Cys Leu Ser Gly Gly Ser His Thr Ser Asp Pro Ala Pro Val His Asn
145                 150                 155                 160

Pro Tyr Arg His Gly Phe Ala Ala Gly Gly Ser Ser Gly Ser Ala
                165                 170                 175

Ala Leu Val Ala Ala Gly Glu Val Asp Leu Ala Val Gly Gly Asp Gln
            180                 185                 190

Gly Gly Ser Ile Arg Ile Pro Ser Ala Phe Cys Gly Thr Tyr Gly Met
            195                 200                 205

Lys Pro Thr His Gly Leu Val Pro Tyr Thr Gly Ile Met Thr Ile Glu
            210                 215                 220

Ala Thr Ile Asp His Ala Gly Pro Ile Thr Arg Asn Val Arg Asp Asn
225                 230                 235                 240

Ala Leu Met Leu Glu Val Met Ala Gly Ala Asp Gly Leu Asp Pro Arg
                245                 250                 255

Gln Ala Ala Pro Gln Val Asp Ala Tyr Cys Asp Tyr Leu Glu Arg Gly
                260                 265                 270

Val Ser Gly Leu Arg Ile Gly Ile Leu Gln Glu Gly Phe Gln Leu Ala
            275                 280                 285

Asn Gln Asp Pro Arg Val Ala Asp Lys Val Arg Gly Ala Ile Ala Arg
            290                 295                 300

Leu Glu Ala Leu Gly Ala Arg Val Glu Glu Val Ser Val Pro Glu His
305                 310                 315                 320

Asn Leu Ala Gly Ser Leu Trp His Pro Ile Gly Cys Glu Gly Leu Thr
                325                 330                 335

Met Gln Met Met His Gly Asn Gly Ala Gly Phe Asn Trp Lys Gly Leu
                340                 345                 350

Tyr Asp Val Gly Leu Leu Asp Lys Gln Ala Gly Trp Arg Glu Gln Ala
            355                 360                 365

Asp Ala Leu Ser Ala Ser Leu Lys Leu Cys Met Phe Val Gly Gln Tyr
            370                 375                 380

Gly Leu Glu Arg Tyr Asn Gly Arg Phe Tyr Ala Lys Ala Gln Asn Ile
385                 390                 395                 400

Ala Arg Phe Ala Arg Ala Gly Tyr Asp Lys Ala Leu Gln Thr Tyr Asp
                405                 410                 415

Leu Leu Val Met Pro Thr Val Pro Ile Ile Ala Gln Pro His Pro Glu
            420                 425                 430

Pro Asp Cys Ser Ile Thr Glu Tyr Val Ala Arg Ala Leu Glu Met Ile
            435                 440                 445
```

Gly Asn Thr Ala Pro Gln Asp Ile Thr Gly His Pro Ala Met Ser Ile
        450                 455                 460

Pro Cys Gly Leu Val Asn Gly Leu Pro Val Gly Leu Met Phe Val Gly
465                 470                 475                 480

Lys His Tyr Ala Glu Gly Thr Ile Tyr Gln Ala Ala Ala Phe Glu
                485                 490                 495

Ala Asp Val Asp Trp Lys Thr Leu
            500

<210> SEQ ID NO 4
<211> LENGTH: 1515
<212> TYPE: DNA
<213> ORGANISM: Artificial Sequence
<220> FEATURE:
<223> OTHER INFORMATION: Isolated from strain KNK AM40

<400> SEQUENCE: 4

```
atggccattg ttcgccctac cctcgaccaa ctgcaggaca tcgctggcca gctgaatatg      60
cagctgacac acgagcaggc agtggaatac ctggcactga tgcagccaag tttcgatgca     120
tatgacctgg tcgacgagtt gccggatttc accccgtcgg tgcgctacga ccgcagttcc     180
ggctaccgcc cgtctaaccc gcaaaacttg ctcaacgcct ggtattacag gaccgaggtg     240
aatggcgccc gtgagggcaa gctggctggc aagactgttg cgcttaaaga caacatcgcc     300
ttggctggcg tcccgatgat gaacggcgcc tcaatccttg aagggtttgt accgtcgttt     360
gacgcaaccg tggtgacccg tttgctagac gccggggcga ccatcctggg caaggcgacc     420
tgtgagcact actgcctctc cggtggcagc cacacctctg atccggcgcc cgtacacaac     480
ccataccggc acggtttcgc tgccggcgga tcctcctccg gaagcgctgc attggtggca     540 gccgcgagg tggacctggc cgttggcggc gatcaaggcg gctcgatccg tatcccttca     600
gcgttctgcg gcacctatgg catgaagccg acccacggtc tggtgcccta caccggaatc     660
atgacgatcg aggccaccat cgaccatgcc ggtcccatca cccgcaacgt gcgtgacaac     720
gcgctgatgc tggaagtcat ggccggtgcc gacgggctcg atcctcgtca ggctgcccct     780
caagtcgacg cctattgcga ctatctggag cgaggtgtga gcggactgcg gatcggcatc     840
ctgcaggaag gcttccagct ggccaaccag gatccacgcg ttgccgacaa ggtacgcggc     900
gccatcgccc gactcgaagc cttgggagct cgcgtcgaag aggtctccgt tcccgagcac     960
aacctggcag gttcgctgtg gcaccccatc ggctgcgaag gctgaccat gcagatgatg    1020 catggcaatg gcgcaggctt taactggaag gggctctacg acgtcggtct gctggataaa    1080
caggccggtt ggcgcgaaca gcggacgca ttatccgcat cgctcaagct gtgcatgttc    1140
gtcggccagt acggtctgga acgctacaac ggtcgtttct acgccaaggc tcagaacatc    1200
gcacgcttcg cccgggccgg ttacgacaag gcactgcaga cctacgacct gctggtcatg    1260
ccgaccgtgc cgatcatcgc ccagcccac cccgaacccg attgttcgat cactgagtac    1320
gtggcccggg cactggaaat gatcggtaac accgcgccgc aggacattac cggccatccg    1380
gccatgtcaa tcccgtgcgg tctggtgaac ggtctgccgg tggggctgat gttcgtcggc    1440
aaacactatg ccgaaggcac gatttaccag gcggcggcag cgttcgaggc cgatgtcgac    1500
tggaagacgt tgtaa                                                      1515
```

<210> SEQ ID NO 5
<211> LENGTH: 504
<212> TYPE: PRT
<213> ORGANISM: Artificial Sequence
<220> FEATURE:
<223> OTHER INFORMATION: Isolated from strain KNK AM1011

<400> SEQUENCE: 5

```
Met Ala Ile Val Arg Pro Thr Leu Asp Gln Leu Gln Asp Ile Ala Gly
1               5                   10                  15

Arg Leu Asn Met Gln Leu Pro His Glu Gln Ala Ala Glu Tyr Leu Ala
            20                  25                  30

Leu Met Gln Pro Ser Phe Asp Ala Tyr Asp Leu Val Asp Glu Leu Pro
        35                  40                  45

Asp Phe Thr Pro Pro Val Arg Tyr Asp Arg Ser Ser Gly Tyr Arg Pro
    50                  55                  60

Ser His Pro Gln Asn Leu Leu Asn Ala Trp Tyr Tyr Arg Thr Glu Val
65                  70                  75                  80

Asn Gly Ala Arg Glu Gly Lys Leu Ala Gly Lys Thr Val Ala Leu Lys
                85                  90                  95

Asp Asn Ile Ala Leu Ala Gly Val Pro Met Met Asn Gly Ala Ser Ile
            100                 105                 110

Leu Glu Gly Phe Val Pro Ser Phe Asp Ala Thr Val Val Thr Arg Leu
        115                 120                 125

Leu Asp Ala Gly Val Thr Ile Leu Gly Lys Ala Thr Cys Glu His Tyr
    130                 135                 140

Cys Leu Ser Gly Gly Ser His Thr Ser Asp Pro Ala Pro Val His Asn
145                 150                 155                 160

Pro Tyr Arg Asn Gly Phe Ala Ala Gly Ser Ser Gly Ser Ala
                165                 170                 175

Ala Leu Val Ala Ala Gly Glu Val Asp Leu Ala Val Gly Gly Asp Gln
            180                 185                 190

Gly Gly Ser Ile Arg Ile Pro Ser Ala Phe Cys Gly Thr Tyr Gly Met
        195                 200                 205

Lys Pro Thr His Gly Leu Val Pro Tyr Thr Gly Ile Met Ala Ile Glu
    210                 215                 220

Ala Thr Ile Asp His Val Gly Pro Ile Thr Arg Asn Val Arg Asp Asn
225                 230                 235                 240

Ala Leu Met Leu Glu Val Met Ala Gly Ala Asp Gly Leu Asp Pro Arg
                245                 250                 255

Gln Ala Ala Pro Gln Val Asp Ala Tyr Cys Asp Tyr Leu Asp Arg Gly
            260                 265                 270

Val Ser Gly Leu Arg Ile Gly Val Leu Gln Glu Gly Phe Gln Leu Ala
        275                 280                 285

Asn Gln Asp Pro Arg Val Ala Asp Lys Val Arg Ser Ala Ile Ala Arg
    290                 295                 300

Leu Glu Ala Leu Gly Ala Arg Val Glu Glu Val Ser Val Pro Glu His
305                 310                 315                 320

Asn Leu Ala Gly Ser Leu Trp His Pro Ile Gly Cys Glu Gly Leu Thr
                325                 330                 335

Met Gln Met Met His Gly Asn Gly Ala Gly Phe Asn Trp Lys Gly Leu
            340                 345                 350

Tyr Asp Val Gly Leu Leu Asp Lys Gln Val Gly Trp Arg Glu Gln Ala
        355                 360                 365

Asp Ala Leu Ser Ala Ser Leu Lys Leu Cys Met Phe Val Gly Gln Tyr
    370                 375                 380

Gly Leu Glu Arg Tyr Tyr Gly Arg Phe Tyr Ala Lys Ala Gln Asn Ile
385                 390                 395                 400
```

```
Ala Arg Phe Ala Arg Ala Gly Tyr Asp Lys Val Leu Glu Thr Tyr Asp
                405                 410                 415

Leu Leu Val Met Pro Thr Val Pro Ile Ile Ala Gln Pro His Pro Glu
            420                 425                 430

Pro Asp Cys Ser Ile Thr Glu Tyr Val Ala Arg Ala Leu Glu Met Ile
            435                 440                 445

Gly Asn Thr Ala Pro Gln Asp Ile Thr Gly His Pro Ala Met Ser Ile
    450                 455                 460

Pro Cys Gly Leu Val Asn Gly Leu Pro Val Gly Leu Met Phe Val Gly
465                 470                 475                 480

Lys His Tyr Ala Glu Gly Thr Ile Tyr Gln Ala Ala Ala Phe Glu
                485                 490                 495

Ala Ala Val Asp Trp Lys Thr Leu
            500
```

<210> SEQ ID NO 6
<211> LENGTH: 1515
<212> TYPE: DNA
<213> ORGANISM: Artificial Sequence
<220> FEATURE:
<223> OTHER INFORMATION: Isolated from strain KNK AM1011

<400> SEQUENCE: 6

```
atggccattg ttcgccctac cctcgatcaa ttgcaggaca tcgctggccg gctgaatatg      60
cagctgcccc atgagcaggc agcggaatac ctggcactta tgcagccaag tttcgacgcc     120
tatgacttgg tcgacgagtt gccggatttc actccgccgg tgcggtacga ccgcagttcg     180
ggctaccgcc cttcacaccc gcagaacctg ctcaacgcct ggtattacag gactgaagtc     240
aatgcgcccc gtgagggcaa gcttgcaggc aagactgttg cgctcaagga caacatcgcc     300
ttggctggcg tcccgatgat gaacggcgcc tcaattctgg aagggtttgt accgtcgttt     360
gacgccaccg tggtgacccg cttgctggac gccggggtca ccattctggg caaggcgacc     420
tgcgagcatt actgcctctc cggtggtagc cacacgtctg atccggcccc cgtacacaac     480
ccataccgga acggtttcgc tgctggaggt tcctcctccg gtagcgctgc attggtggca     540
gccggcgagg tggacctggc ggttggcggc gatcaaggcg gttcgatccg catcccttca     600
gcgttctgcg gcacctatgg catgaagccg acccacggtt tggtgcctta caccgggatc     660
atggcgatcg aagccaccat cgaccatgtc ggtcccatca cccgcaacgt acgtgacaac     720
gcgctgatgc tggaagtcat ggccggtgcc gatggactcg atcctcgcca ggccgcacct     780
caggtcgacg cctactgcga ctacctggat cgaggtgtga gcgggctccg gatcggcgtc     840
ctgcaggaag gcttccagct ggccaatcag gatccacgcg ttgccgacaa ggtacgcagc     900
gccatcgccc gccttgaggc tttgggcgct cgcgtcgagg aagtctctgt tccagagcac     960
aatctggcgg ttcgctgtg gcaccccatc ggctgcgaag gcctgaccat gcagatgatg    1020
catggcaatg gcgcaggttt taactggaag ggtctctacg acgtcggcct gctggataaa    1080
caggtcggtt ggcgcgaaca agcggacgct ttatccgcgt cgctcaagct ctgcatgttc    1140
gtcggccagt acgcctgga acgctactac ggtcgtttct acgccaaggc acagaacatc    1200
gcacgcttcg cccgggccgg ttatgacaag gtactggaga cctacgacct actggtcatg    1260
ccgaccgtac cgatcatcgc ccagcccac cccgaacccg attgttcgat cactgagtac    1320
gtggcccggg cgctggaaat gatcggcaac acagcgcctc aggacattac cggtcatccg    1380
gccatgtcga tcccatgcgg tctggtgaac ggtctgccgg tggggctgat gttcgttggc    1440
```

```
aaacactatg ccgaaggcac gatttaccag gcagcggcag cgttcgaggc cgccgtcgac    1500
tggaagacgt tgtaa                                                     1515
```

<210> SEQ ID NO 7
<211> LENGTH: 504
<212> TYPE: PRT
<213> ORGANISM: Artificial Sequence
<220> FEATURE:
<223> OTHER INFORMATION: Isolated from strain KNK AM250

<400> SEQUENCE: 7

Met Ala Ile Val Arg Pro Thr Leu Asp Gln Leu Gln Asp Ile Ala Gly
1               5                   10                  15

Arg Leu Asn Met Gln Leu Thr His Glu Gln Ala Ala Glu Tyr Leu Ala
            20                  25                  30

Leu Met Gln Pro Ser Phe Asp Ala Tyr Asp Leu Val Asp Glu Leu Pro
        35                  40                  45

Asp Phe Thr Pro Pro Val Arg Tyr Asp Arg Ser Ser Gly Tyr Arg Pro
    50                  55                  60

Ser Asn Ser Gln Asn Leu Leu Asn Ala Trp Tyr Tyr Arg Thr Glu Val
65                  70                  75                  80

Asn Gly Ala Arg Glu Gly Lys Leu Ala Gly Lys Thr Val Ala Leu Lys
                85                  90                  95

Asp Asn Ile Ser Leu Ala Gly Val Pro Met Met Asn Gly Ala Ala Pro
            100                 105                 110

Leu Glu Gly Phe Val Pro Lys Phe Asp Ala Thr Val Val Thr Arg Leu
        115                 120                 125

Leu Asp Asp Gly Val Thr Ile Leu Gly Lys Ala Thr Cys Glu His Tyr
    130                 135                 140

Cys Leu Ser Gly Gly Ser His Thr Ser Asp Pro Ala Pro Val His Asn
145                 150                 155                 160

Pro Tyr Arg His Gly Phe Ala Ala Gly Gly Ser Ser Gly Cys Ala
                165                 170                 175

Ala Leu Val Ala Ala Gly Glu Val Asp Leu Ala Val Gly Gly Asp Gln
            180                 185                 190

Gly Gly Ser Ile Arg Ile Pro Ser Ala Phe Cys Gly Thr Tyr Gly Met
        195                 200                 205

Lys Pro Thr His Gly Leu Val Pro Tyr Thr Gly Ile Met Ala Ile Glu
    210                 215                 220

Ala Thr Ile Asp His Val Gly Pro Ile Thr Arg Asn Val Arg Asp Asn
225                 230                 235                 240

Ala Leu Met Leu Glu Val Met Ala Gly Ala Asp Gly Leu Asp Pro Arg
                245                 250                 255

Gln Ala Ala Pro Gln Val Asp Ala Tyr Cys Asp Tyr Leu Glu Arg Gly
            260                 265                 270

Val Ser Gly Leu Arg Ile Gly Ile Leu Gln Glu Gly Phe Gln Leu Ala
        275                 280                 285

Asn Gln Asp Pro Arg Val Ala Asp Lys Val Arg Ser Ala Ile Ala Arg
    290                 295                 300

Leu Glu Val Leu Gly Ala Arg Val Glu Glu Val Ser Val Pro Glu His
305                 310                 315                 320

Asn Leu Ala Gly Ser Leu Trp His Pro Ile Gly Cys Glu Gly Leu Thr
                325                 330                 335

Met Gln Met Met His Gly Asn Gly Ala Gly Phe Asn Trp Lys Gly Leu

```
                340             345             350
Tyr Asp Val Gly Leu Leu Asp Lys Gln Thr Gly Trp Arg Asp Gln Ala
            355                 360                 365
Asp Ala Leu Ser Ala Ser Leu Lys Leu Cys Met Phe Val Gly Gln Tyr
        370                 375                 380
Gly Leu Glu His Tyr Asn Gly Arg Phe Tyr Ala Lys Ala Gln Asn Ile
385                 390                 395                 400
Ala Arg Phe Ala Arg Ala Gly Tyr Asp Lys Ala Leu Glu Thr Tyr Asp
                405                 410                 415
Leu Leu Val Met Pro Thr Val Pro Ile Ile Ala Gln Pro His Pro Glu
            420                 425                 430
Pro Asp Cys Ser Ile Thr Glu Tyr Val Ala Arg Ala Leu Glu Met Ile
        435                 440                 445
Gly Asn Thr Ala Pro Gln Asp Ile Thr Gly His Pro Ala Met Ser Ile
    450                 455                 460
Pro Cys Gly Leu Val Asp Gly Leu Pro Val Gly Leu Met Phe Val Gly
465                 470                 475                 480
Lys His Tyr Ala Glu Gly Thr Ile Tyr Gln Ala Ala Ala Phe Glu
                485                 490                 495
Ala Thr Val Asp Trp Lys Thr Leu
            500

<210> SEQ ID NO 8
<211> LENGTH: 1515
<212> TYPE: DNA
<213> ORGANISM: Artificial Sequence
<220> FEATURE:
<223> OTHER INFORMATION: Isolated from strain KNK AM250

<400> SEQUENCE: 8
atggccattg ttcgccctac cctcgaccaa ctgcaggaca tcgctggccg gctgaatatg      60
cagctgaccc acgagcaggc agcggaatac ctggcactta tgcagccaag tttcgatgca     120
tatgacctgg tcgacgagtt gccggacttc accccgccgg tgcgctacga ccgcagttcg     180
ggctaccgcc cgtcaaactc gcaaaacctg ctcaatgcct ggtattacag gactgaggtg     240
aatggcgccc gtgagggcaa acttgctggc aagactgttg cgctcaagga caacatctcc     300
ctggctggcg tcccgatgat gaacggcgcc gccccactgg aaggcttcgt accgaaattc     360
gacgctaccg tggtgacccg tttgctggac gacggggtca ccattctggg caaggcgacc     420
tgtgaacact actgcctctc cggtggcagc cacacgtctg atccagcgcc cgtacataac     480
ccgtatcggc acggtttcgc tgctggcgga tcctcctcgg gctgcgctgc gttagtagcc     540
gccggcgagg tggacctggc ggttggcggt gatcagggtg gatccatccg catcccttca     600
gcgttctgcg gcacctatgg catgaagccg actcacggtt tggtgcctta caccggcatc     660
atggcgatcg aagccaccat cgaccatgtc ggtcccatca cccgcaacgt gcgtgacaac     720
gcactgatgc tggaagtcat ggccggtgcc gacggactcg accctcgcca ggccgctcct     780
caggtcgacg cctactgcga ttatctggag cgaggtgtga gcgggctgcg gatcggcatc     840
ctgcaggaag gctttcagct ggccaatcag gatccacgtg ttgccgacaa ggtgcgcagc     900
gccatcgccc ggcttgaggt cctgggcgct cgcgtcgagg aagtctccgt ccccgagcac     960
aacctggcgg ttccctgtg gcaccccatc ggctgcgaag gcctgaccat gcagatgatg    1020
catggcaatg gcgcaggctt taactggaaa ggcctctatg acgtcggcct gctggataaa    1080
cagaccggct ggcgcgacca agcggacgca ttgtctgcgt cgctcaaact gtgcatgttc    1140
```

| | |
|---|---|
| gtcggccaat acggcctgga acattacaac ggtcgcttct acgccaaggc tcagaacatc | 1200 |
| gcacgcttcg cccgggccgg ttacgacaag gcactggaga cctatgacct tctggtcatg | 1260 |
| ccgaccgtgc cgatcattgc ccagcctcac ccagaacccg attgttcgat caccgagtac | 1320 |
| gtggcccgtg cgctggaaat gatcggcaac accgcgccgc aggacattac tggccatccg | 1380 |
| gccatgtcga tcccgtgtgg tctggtggac ggcctgcccg tcgggctgat gttcgttggc | 1440 |
| aagcactatg ccgaaggcac gatttaccag gcggcggcag cgttcgaggc cactgtcgac | 1500 |
| tggaagacgt tgtaa | 1515 |

```
<210> SEQ ID NO 9
<211> LENGTH: 20
<212> TYPE: DNA
<213> ORGANISM: Artificial Sequence
<220> FEATURE:
<223> OTHER INFORMATION: Synthetic Primer-1
<220> FEATURE:
<221> NAME/KEY: misc_feature
<222> LOCATION: (9)..(9)
<223> OTHER INFORMATION: n represents a, t, g, or c
<220> FEATURE:
<221> NAME/KEY: misc_feature
<222> LOCATION: (12)..(12)
<223> OTHER INFORMATION: n represents a, t, g, or c

<400> SEQUENCE: 9
```

| | |
|---|---|
| atgcarytna cncaygarca | 20 |

```
<210> SEQ ID NO 10
<211> LENGTH: 20
<212> TYPE: DNA
<213> ORGANISM: Artificial Sequence
<220> FEATURE:
<223> OTHER INFORMATION: Synthetic Primer-2
<220> FEATURE:
<221> NAME/KEY: misc_feature
<222> LOCATION: (6)..(6)
<223> OTHER INFORMATION: n represents a, t, g, or c

<400> SEQUENCE: 10
```

| | |
|---|---|
| ccrttnccrt gcatcatytg | 20 |

```
<210> SEQ ID NO 11
<211> LENGTH: 30
<212> TYPE: DNA
<213> ORGANISM: Artificial Sequence
<220> FEATURE:
<223> OTHER INFORMATION: Synthetic Primer-3

<400> SEQUENCE: 11
```

| | |
|---|---|
| accccatcgg ctgcgaaggc ctgaccatgc | 30 |

```
<210> SEQ ID NO 12
<211> LENGTH: 30
<212> TYPE: DNA
<213> ORGANISM: Artificial Sequence
<220> FEATURE:
<223> OTHER INFORMATION: Synthetic Primer-4

<400> SEQUENCE: 12
```

| | |
|---|---|
| gggcgccatt cacctcagtc ctgtaatacc | 30 |

```
<210> SEQ ID NO 13
<211> LENGTH: 42
<212> TYPE: DNA
```

```
<213> ORGANISM: Artificial Sequence
<220> FEATURE:
<223> OTHER INFORMATION: Synthetic Primer-5

<400> SEQUENCE: 13
cggaattcta aggaggttac aatggccatt gttcgcccta cc          42

<210> SEQ ID NO 14
<211> LENGTH: 30
<212> TYPE: DNA
<213> ORGANISM: Artificial Sequence
<220> FEATURE:
<223> OTHER INFORMATION: Synthetic Primer-6

<400> SEQUENCE: 14
gcagagctct tacaacgtct tccagtcgac                         30

<210> SEQ ID NO 15
<211> LENGTH: 26
<212> TYPE: DNA
<213> ORGANISM: Artificial Sequence
<220> FEATURE:
<223> OTHER INFORMATION: Synthetic Primer

<400> SEQUENCE: 15
caargcvacy tgygagcayt actgcc                             26

<210> SEQ ID NO 16
<211> LENGTH: 26
<212> TYPE: DNA
<213> ORGANISM: Artificial Sequence
<220> FEATURE:
<223> OTHER INFORMATION: Synthetic Primer

<400> SEQUENCE: 16
gcsccrttgc crtgcatcat ctgcat                             26
```

VECTOR, A TRANSFORMANT AND A METHOD TO PRODUCE A POLYPEPTIDE HAVING ACTIVITY TO SELECTIVELY HYDROLYZE A (R)-TROPIC ACID AMIDE IN A RACEMIC MIXTURE

TECHNICAL FIELD

The present invention relates to a novel polypeptide having activity of (R)-selectively hydrolyzing a racemic tropic acid amide, DNA encoding the polypeptide, a vector containing the DNA, a transformant prepared by transformation with the vector, and a method for producing an optically active carboxylic acid amide and an optically active carboxylic acid using them.

BACKGROUND ART

Optically active tropic acid is a useful compound as a synthetic raw material or an intermediate for biologically active alkaloids, pharmaceutical products, and the like. Regarding methods for obtaining an optically active tropic acid, a method that involves reacting a racemic tropic acid with luciferase, ATP, divalent metal ions, and CoA to perform optical resolution (Patent Document 1), a method that involves the optical resolution of an racemic tropic acid butyl ester using *Candida antarctica* lipase B (CAL-B) (Non-patent Document 1), and a method that involves the optical resolution of a racemic tropic acid ester using *Klebsiella oxytoca*-derived esterase (Non-patent Document 2) are conventionally known. However, no method for obtaining an optically active tropic acid by asymmetrically hydrolyzing a racemic tropic acid amide is known.

PRIOR ART DOCUMENTS

Patent Document

Patent Document 1: JP Patent Publication (Kokai) No. 2007-29017 A

Non-patent Documents

Non-patent Document 1: Tetrahedron: Asymmetry 16: 2005, 3892-3896
Non-patent Document 2: Journal of Molecular Catalysis B: Enzymatic 57, 158-163 (2009)

SUMMARY OF THE INVENTION

Problem to be Solved by the Invention

An object of the present invention is to provide a means for producing an optically active tropic acid that is a useful compound as a synthetic raw material or an intermediate for pharmaceutical products and the like.

Means for Solving the Problem

As a result of intensive studies to achieve the above object, the present inventors have isolated and purified an amidase enzyme capable of (R)-selectively hydrolyzing a racemic tropic acid amide from an KNK AM 38 strain isolated by the present inventors from soil, and thus have obtained DNA encoding the enzyme. They have further confirmed that an amidase-rich transformant produced by using the thus obtained DNA allows the hydrolytic reaction of a tropic aid amide to proceed in a highly stereoselective manner. Furthermore, PCR has been performed using primers designed based on the nucleotide sequence of the above KNK AM 38 strain-derived DNA and a known nucleotide sequence having high homology with this nucleotide sequence, and the chromosomal DNAs of 3 other microorganisms isolated from soil (the KNK AM 40 strain, the KNK AM 1011 strain, the KNK AM 250 strain) as templates, thus enabling DNAs encoding amidase enzymes having activity equivalent to the hydrolytic activity of the KNK AM 38 strain to be obtained. The nucleotide sequences of the four thus obtained DNAs have not yet been registered in DNA databases including the DDBJ, and thus have been confirmed to be novel sequences. The present invention has been completed based on these findings.

The present invention encompasses the following [1] to [8].

[1] A polypeptide, which is any one of the following polypeptides (a) to (c):
(a) a polypeptide consisting of the amino acid sequence shown in SEQ ID NO: 1, 3, 5, or 7;
(b) a polypeptide consisting of an amino acid sequence that has a deletion, an insertion, a substitution and/or an addition of 1 or a plurality of amino acids with respect to the amino acid sequence shown in SEQ ID NO: 1, 3, 5, or 7, and having activity to (R)-selectively hydrolyze a racemic tropic acid amide; and
(c) a polypeptide consisting of an amino acid sequence that has 80% or more sequence identity with the amino acid sequence shown in SEQ ID NO: 1, 3, 5, or 7, and having activity to (R)-selectively hydrolyze a racemic tropic acid amide.

[2] DNA, encoding the polypeptide according to [1].
[3] DNA, which is any one of the following DNAs (d) to (g):
(d) DNA consisting of the nucleotide sequence shown in SEQ ID NO: 2, 4, 6, or 8;
(e) DNA consisting of a nucleotide sequence that has 80% or more sequence identity with the nucleotide sequence shown in SEQ ID NO: 2, 4, 6, or 8, and encoding a polypeptide that has activity to (R)-selectively hydrolyze a racemic tropic acid amide;
(f) DNA hybridizing under stringent conditions to DNA consisting of a nucleotide sequence complementary to the nucleotide sequence shown in SEQ ID NO: 2, 4, 6, or 8, and encoding a polypeptide that has activity to (R)-selectively hydrolyze a racemic tropic acid amide; and
(g) DNA consisting of a nucleotide sequence that has a deletion, an insertion, a substitution and/or an addition of one or a plurality of nucleotides with respect to the nucleotide sequence shown in SEQ ID NO: 2, 4, 6, or 8, and encoding a polypeptide that has activity to (R)-selectively hydrolyze a racemic tropic acid amide.

[4] A vector, containing the DNA according to [2] or [3].
[5] A transformant, which is obtained by the transformation of a host cell with the vector according to [4].
[6] The transformant according to [5], wherein the host cell is *Escherichia coli*.
[7] A method for producing the polypeptide according to [1], comprising culturing the transformant according to [5] or [6] in a medium, and then collecting the expressed polypeptide from the resulting culture product.
[8] A method for producing an optically active carboxylic acid and/or an optically active carboxylic acid amide, comprising causing the polypeptide according to [1] or the transformant according to [5] or

[6] to act on an enantiomeric mixture of a carboxylic acid amide represented by the following formula (I):

[Chemical formula 1]

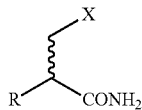

(I)

(wherein X denotes a hydroxyl group or an amide group, and R denotes an alkyl group that may have a substituent, an alkenyl group that may have a substituent, an alkynyl group that may have a substituent, an aryl group that may have a substituent, or an aralkyl group that may have a substituent), and
generating an (R)- or (S)-carboxylic acid represented by the following formula (II):

[Chemical formula 2]

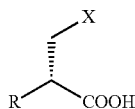

(II)

(wherein X and R are as defined above) and/or an (S)- or (R)-carboxylic acid amide represented by the following formula (III):

[Chemical formula 3]

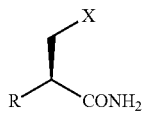

(III)

(wherein X and R are as defined above).

This application claims priority of Japanese patent application No. 2011-214381 filed on Sep. 29, 2011, and encompasses the contents in the description and/or drawings of the patent application.

Effect of the Invention

According to the present invention, a novel polypeptide having activity to (R)-selectively hydrolyze a racemic tropic acid amide is provided. With the use of the polypeptide of the present invention, an optically active carboxylic acid and an optically active carboxylic acid amide, such as an optically active tropic acid, which are useful as synthetic raw materials and intermediates for pharmaceutical products and the like can be produced with high optical purity and high yield.

MODES FOR CARRYING OUT THE INVENTION

1. Novel Amidase and Polypeptide

The amidase of the present invention is a polypeptide having activity to (R)-selectively hydrolyze a racemic tropic acid amide, which consists of the amino acid sequence shown in SEQ ID NO: 1, 3, 5, or 7. The polypeptide consisting of the amino acid sequence of SEQ ID NO: 1 is a polypeptide isolated from the KNK AM 38 strain. The polypeptides consisting of the amino acid sequences shown in SEQ ID NO: 3, 5, and 7 are polypeptides isolated from the KNK AM 40 strain, the KNK AM 1011 strain, and the KNK AM 250 strain, respectively, which have the activity substantially equivalent to the above activity. The term "substantially equivalent" refers to, for example, 90% or more, preferably 95% or more, and more preferably 98% or more activity with respect to the above activity of the polypeptide consisting of the amino acid sequence of SEQ ID NO: 1.

Furthermore, examples of the amidase of the present invention include polypeptides homologous to the polypeptide consisting of the amino acid sequence shown in SEQ ID NO: 1, 3, 5, or 7, as long as they have activity to (R)-selectively hydrolyze a racemic tropic acid amide. An example of such a homologous polypeptide is a polypeptide consisting of an amino acid sequence that has a deletion, an insertion, a substitution and/or an addition of 1 or a plurality of amino acids with respect to the amino acid sequence shown in SEQ ID NO: 1, 3, 5, or 7, and having activity to (R)-selectively hydrolyze a racemic tropic acid amide. Here, the number of "a plurality of amino acids" refers to the number of amino acids that can be deleted, inserted, substituted, and/or added by a known method for preparing a mutant protein, such as site-directed mutagenesis. This number of amino acids is not limited as long as the above-mentioned activity is retained, and is 30 or less, preferably 20 or less, more preferably 10 or less, further preferably 7 or less, and particularly preferably 5 or less, for example.

The above deletion, insertion, substitution and/or addition of amino acids can be introduced into the amino acid sequence shown in SEQ ID NO: 1, 3, 5, or 7 by a known technique such as site-directed mutagenesis (Nucleic Acids Res (1982) 10: 6487; Methods in Enzymol (1983) 100: 448; Molecular Cloning 2nd Edt., Cold Spring Harbor Laboratory Press (1989); PCR A Practical Approach, IRL Press (1991) pp. 200) or a method according thereto.

Another example of the above homologous polypeptide is a polypeptide consisting of an amino acid sequence that has 80% or more sequence identity with the amino acid sequence shown in SEQ ID NO: 1, 3, 5, or 7, and having activity to (R)-selectively hydrolyze a racemic tropic acid amide. Here, the term "80% or more sequence identity" refers to preferably 85% or more, more preferably 90% or more, further preferably 95% or more, and most preferably 98% or more sequence identity. Sequence identity is found by comparing and analyzing two amino acid sequences using the BLAST homology search program (W. R. Pearson & D. J. Lipman P.N.A.S. (1988) 85: 2444-2448) and thus is represented by the identity (percentage) with respect to the whole sequence.

The polypeptide of the present invention can be obtained by a method that involves chemically synthesizing the polypeptide based on its amino acid sequence, in vitro transcription from an expression vector, or a method that involves the isolation and purification of the expression product of cells transformed with an expression vector, for example.

The polypeptide can be chemically synthesized, by a known chemical synthesis method such as the Fmoc method (fluorenylmethyloxycarbonyl method), or the tBoc method (t-butyloxycarbonyl method).

When the polypeptide is expressed by in vitro translation, the polypeptide can be produced in vitro by adding an expression vector having an RNA polymerase promoter to an in vitro translation system such as a rabbit reticulocyte lysate or a wheat germ extract containing RNA polymerase corresponding to the promoter. Examples of such an RNA polymerase promoter include T7, T3, and SP6. Moreover, examples of vectors containing the RNA polymerase promoters include pKA1, pCDM8, pT3/T7 18, pT7/3 19, and pBluescript II.

Furthermore, when the polypeptide is isolated and purified as an expression product of cells transformed with an expression vector, procedures for isolation and purification are described below under the "transformant" section and are summarized as follows. First, a nucleotide sequence encoding the polypeptide is determined based on each of the above amino acid sequences, and then a DNA fragment consisting of the nucleotide sequence is obtained. Next, when the polypeptide is expressed using *Escherichia coli*, for example, the above DNA fragment is incorporated into an expression vector having an origin that is replicable within *Escherichia coli*, a promoter, a ribosome binding site, a DNA cloning site, a terminator, and the like, thereby preparing an expression vector. Host cells are transformed with the expression vector, and thus transformed cells expressing the polypeptide can be obtained. The transformant is cultured, and thus the polypeptide of interest produced in the culture product can be obtained.

2. DNA

The DNA of the present invention may be any DNA that encodes a polypeptide having activity to (R)-selectively hydrolyze a racemic tropic acid amide, and can express the polypeptide of "1." within host cells into which it has been introduced according to a method described later. The DNA may also contain an arbitrary untranslated region. A specific example of the DNA of the present invention is DNA consisting of the nucleotide sequence shown in SEQ ID NO: 2, 4, 6, or 8.

The DNA of the present invention encoding a polypeptide having activity to (R)-selectively hydrolyze a racemic tropic acid amide can be obtained by the following method, for example. First, an N-terminal amino acid sequence of a polypeptide purified from a microorganism having activity to (R)-selectively hydrolyze a racemic tropic acid amide, such as the above KNK AM38 strain, is determined by a gas phase protein sequencer or the like. Also, protease such as lysylendopeptidase is caused to act on the purified polypeptide to digest it into a polypeptide of an appropriate size, the resultant is subjected to HPLC or the like, the thus obtained polypeptide is purified, and thus the internal amino acid sequence is determined according to a method similar to the above. DNA primers designed based on the thus obtained N-terminal amino acid sequence and the internal amino acid sequence are synthesized. Next, chromosomal DNA is isolated from a microorganism serving as an origin for the polypeptide. The chromosomal DNA is obtained by lysing and treating cultured cells with a surfactant, cetyltrimethylammonium bromide (CTAB), chloroform, phenol, or the like, precipitating the extracted DNA with isopropanol, and then washing with ethanol the precipitate obtained by centrifugation (for example, see Current Protocols in Molecular Biology (Greene Publishing Associates and Wiley-Interscience)). PCR is performed using the chromosomal DNA as a template and the above DNA primers, and thus a portion of the DNA of interest can be obtained. Next, DNA fragments encoding the N-terminal portion and the C-terminal portion of the previously obtained partial gene can be obtained by an inverse PCR method (for example, see Nucleic Acids Res. 16, 8186 (1988)). After the determination of the nucleotide sequences of the DNA fragments, DNA primers are prepared based on each of the nucleotide sequences of a portion assumed to be located upstream of the N-terminus of and a portion assumed to be located downstream of the C-terminus of the polypeptide. PCR is further performed using the DNA primers and the previously obtained chromosomal DNA as a template, and thus DNA encoding the polypeptide of interest can be obtained.

Examples of the DNA of the present invention include DNA homologous to the DNA consisting of the nucleotide sequence shown in SEQ ID NO: 2, 4, 6, or 8, as long as it has activity to (R)-selectively hydrolyze a racemic tropic acid amide.

Examples of such homologous DNA include: DNA consisting of a nucleotide sequence that has 80% or more sequence identity with the nucleotide sequence shown in SEQ ID NO: 2, 4, 6, or 8, and encoding a polypeptide that has activity to (R)-selectively hydrolyze a racemic tropic acid amide; DNA hybridizing under stringent conditions to DNA consisting of a nucleotide sequence complementary to the nucleotide sequence shown in SEQ ID NO: 2, 4, 6, or 8, and encoding a polypeptide that has activity to (R)-selectively hydrolyze a racemic tropic acid amide; and DNA consisting of a nucleotide sequence that has a deletion, an insertion, a substitution and/or an addition of 1 or a plurality of nucleotides with respect to the nucleotide sequence shown in SEQ ID NO: 2, 4, 6, or 8, and encoding a polypeptide that has activity to (R)-selectively hydrolyze a racemic tropic acid amide.

The above term "80% or more sequence identity" refers to preferably 85% or more, more preferably 90% or more, further preferably 95% or more, and most preferably 98% or more sequence identity.

Moreover, the term "DNA hybridizing under stringent conditions to DNA consisting of a nucleotide sequence complementary to the nucleotide sequence shown in SEQ ID NO: 2, 4, 6, or 8" refers to DNA that is obtained under stringent conditions by colony hybridization, plaque hybridization, Southern hybridization or the like using DNA consisting of a nucleotide sequence complementary to the nucleotide sequence shown in SEQ ID NO: 2, 4, 6, or 8, as a probe.

The above term "stringent conditions" refers to conditions wherein namely a specific hybrid is formed, but no nonspecific hybrid is formed. Examples of such conditions include conditions wherein the complementary strand of DNA consisting of a nucleotide sequence having high sequence identity as described above hybridizes to, but the complementary strand of a nucleic acid having homology lower than the above does not hybridize to the nucleotide sequence shown in SEQ ID NO: 2, 4, 6, or 8. Persons skilled in the art can adequately select the above stringent hybridization conditions in reference to Sambrook et al., Molecular Cloning, A Laboratory Manual, 3rd Ed., Cold Spring Harbor Laboratory (2001). An example of such conditions is as follows. After prehybridization is performed overnight at 42° C. in a hybridization solution containing 25% formamide (under more stringent conditions, 50% formamide), 4×SSC, 50 mM HEPES (pH7.0), a 10×Denhardt's solution, and 20 µg/ml denatured salmon sperm DNA, hybridization is performed by adding a labeled probe, and then maintaining the resultant at 42° C. overnight. Wash solutions and temperature conditions during the subsequent washing are about "1×SSC, 0.1% SDS, and 37° C.", and under more stringent conditions, about "0.5×SSC, 0.1% SDS, and 42° C.," and under even more stringent conditions, about "0.2× SSC, 0.1% SDS, and 65° C." Here, an SSC solution having a 1-fold concentration (1× SSC) is composed of 150 mM sodium chloride and 15 mM sodium citrate. The higher the temperature and the lower the salt concentration, the higher the stringency. Thus, the gene with even higher identity can be isolated.

The combinations of the above SSC, SDS and temperature conditions are merely examples. Persons skilled in the art can realize stringency similar to the above by adequately combining the above or other elements (e.g., probe concentration, probe length, and the time for hybridization reaction) that determine the stringency of hybridization.

Also, regarding the above expression "a nucleotide sequence that has a deletion, an insertion, a substitution and/or an addition of 1 or a plurality of nucleotides," the number of nucleotides that may be deleted, inserted, substituted and/or added is not limited, as long as the polypeptide encoded by the DNA does not lose the above activity, and is preferably 200 nucleotides or less, more preferably 150 nucleotides or less, further preferably 100 nucleotides or less, and most preferably 50 nucleotides or less.

The above homologous DNA can be obtained by introducing a mutation into the nucleotide sequence shown in SEQ ID NO: 2, 4, 6, or 8 by a known technique such as site-directed mutagenesis (Nucleic Acids Res (1982) 10: 6487; Methods in Enzymol (1983) 100: 448; Molecular Cloning 2nd Edt., Cold Spring Harbor Laboratory Press (1989); PCR A Practical Approach, IRL Press (1991) pp. 200) or a method according thereto. For example, a mutagenesis kit using site-directed mutagenesis (e.g., Mutant-K (TAKARA) or Mutant-G (TAKARA)), or a LA PCR in vitro Mutagenesis series kit (TAKARA) can be used.

Gene manipulation such as the above DNA isolation, vector construction (described later), and transformation, which are described in the present specification, can be performed by methods described in a reference such as "Molecular Cloning 2nd Edition (Cold Spring Harbor Laboratory Press, 1989), Current Protocols in Molecular Biology (Grene Publishing Associates and Wiley-Interscience)" unless otherwise specified.

3. Vector

The vector of the present invention is not particularly limited, as long as it can express a polypeptide encoded by the above DNA within appropriate host cells. Examples of such a vector include a plasmid vector, a phage vector, and a cosmid vector. Furthermore, a shuttle vector that enables gene exchange with another host strain can also be used herein.

Such a vector generally contains regulatory factors such as a lacUV5 promoter, a trp promoter, a trc promoter, a tac promoter, 1pp promoter, a tufB promoter, a recA promoter, and a pL promoter, and can be preferably used as an expression vector containing an expression unit operably linked to the DNA of the present invention. For example, pUCN18 can be preferably used. Plasmid pUCN18 is prepared by modifying the 185$^{th}$ T of pUC18 (Takara Bio Inc., GenBank Accession No. L09136) to A by PCR, so as to disrupt the Nde I site, and further modifying the 471-472$^{nd}$ GC to TG, so as to introduce a new Nde I site.

The term "regulatory factor" refers to a nucleotide sequence having a functional promoter and an arbitrary related transcriptional element (e.g., enhancer, CCAAT box, TATA box, and SPI site). The above term "operably linked" means that various regulatory elements regulating gene expression such as a promoter and an enhancer are ligated to a gene so that they can function within the host cells. Types and kinds of regulatory factor can be varied depending on the host, which is a matter known by persons skilled in the art.

Examples of host cells as used herein include bacteria, yeast, filamentous bacteria, plant cells, and animal cells. Bacteria are preferred in terms of introduction and expression efficiency, and *Escherichia coli* is particularly preferred.

A vector containing the DNA can be introduced into host cells by a known method such as electroporation, a calcium phosphate method, a liposome method, and a DEAE dextran method. When *Escherichia coli* is used as host cells, for example, the vector can be introduced into host cells using commercially available *Escherichia coli* HB101 competent cells (Takara Bio Inc.).

4. Transformant

The "transformant" of the present invention can be obtained by incorporating DNA encoding the polypeptide of the present invention into the above vector, and then introducing the vector into host cells. In addition, examples of the "transformant" of the present invention naturally include cultured cells and treated products thereof. Here, the term "treated products thereof" refers to, for example, cells treated with a surfactant or an organic solvent, dried cells, disrupted cells, a crude extract of cells, and these cells immobilized by a known means. These treated products can be used for the reaction of the present invention, as long as activity to (R)-selectively hydrolyze a racemic tropic acid amide remains.

The transformant of the present invention can be cultured using a general liquid nutritional medium containing a carbon source, a nitrogen source, an inorganic salt, an organic nutrient, and the like, as long as host cells used for transformation grow and the polypeptide of the present invention is produced.

The polypeptide that is expressed by the transformant can be isolated and purified using known separation procedures in combination. Examples of such procedures include treatment with a denaturing agent such as urea or a surfactant, ultrasonication, enzymatic digestion, salting-out, solvent precipitation, dialysis, centrifugation, ultrafiltration, gel filtration, SDS-PAGE, isoelectric point electrophoresis, ion exchange chromatography, hydrophobic chromatography, affinity chromatography, and reverse phase chromatography.

5. Method for Producing Optically Active Carboxylic Acid Amide and Optically Active Carboxylic Acid According to the present invention, a method for producing an optically active carboxylic acid and/or an optically active carboxylic acid amide is provided, which comprises causing the above polypeptide or transformant to act on an enantiomeric mixture of a carboxylic acid amide represented by the following formula (I):

[Chemical formula 4]

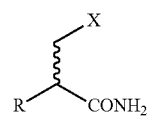

(I)

(wherein X denotes a hydroxyl group or an amide group, and R denotes an alkyl group that may have a substituent, an alkenyl group that may have a substituent, an alkynyl group that may have a substituent, an aryl group that may have a substituent, or an aralkyl group that may have a substituent), and
generating an (R)- or (S)-carboxylic acid represented by the following formula (II):

[Chemical formula 5]

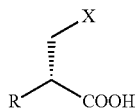

(II)

(wherein X and R are as defined above) and/or an (S)- or (R)-carboxylic acid amide represented by the following formula (III):

[Chemical formula 6]

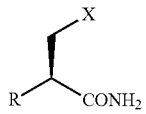

(III)

(wherein X and R are as defined above).

The term "alkyl group" represented by "R" in the above formula (I) generally refers to a C1-8 alkyl group, such as a methyl group, an ethyl group, an n-propyl group, an isopropyl group, an n-butyl group, a sec-butyl group, an isobutyl group, a tert-butyl group, an n-pentyl group, an n-hexyl group, an n-heptyl group, and an n-octyl group.

The term "alkenyl group" represented by "R" in the above formula (I) generally refers to a C2-8 alkenyl group, such as an ethenyl group, a propenyl group, an n-butenyl group, an i-butenyl group, a sec-butenyl group, a pentenyl group, a hexenyl group, a heptenyl group, and an octenyl group.

The term "alkynyl group" represented by "R" in the above formula (I) generally refers to a C2-8 alkynyl group, such as an ethynyl group, a propynyl group, a butynyl group, a pentynyl group, a hexynyl group, a heptinyl group, and an octinyl group.

The term "aryl group" represented by "R" in the above formula (I) generally refers to a C6-14 aryl group, such as a phenyl group, a naphthyl group, an anthracenyl group, a phenanthrenyl group, and a biphenyl group.

The term "aralkyl group" that is the above R group generally refers to a C6-8 aralkyl group, such as a benzyl group, a phenethyl group, and a naphthylmethyl group.

The above alkyl group, alkenyl group, alkynyl group, aryl group, and aralkyl group may have a substituent. Examples of a substituent include a halogen atom, a hydroxyl group, an amino group, and a nitro group.

Specific examples of a carboxylic acid amide serving as a substrate represented by the above formula (I) include a tropic acid amide, a 3-hydroxyisobutyric acid amide, a 2-hydroxymethylvaleric acid amide, a 2-hydroxymethylhexanoic acid amide, a 2-benzyl-3-hydroxypropionic acid amide, a 2-cyclohexyl-3-hydroxypropionic acid amide, and a 3-benzyl-2-hydroxypropionic acid amide. Not only such racemic amides, but also enantiomer mixtures can also be used herein.

An aqueous solvent may be used for reaction, and an aqueous solvent and an organic solvent may be mixed and then used. Examples of an organic solvent include toluene, ethyl acetate, n-butyl acetate, hexane, isopropanol, diisopropyl ether, methanol, acetone, and dimethylsulfoxide. Reaction is performed at a temperature between 10° C. and 70° C. The pH of the reaction solution is maintained at 4 to 10, for example. Reaction can be performed in a batch mode or a continuous mode. In the case of the batch mode, a reaction substrate is added at a concentration ranging from 0.1% to 70% (w/v) at the time of preparation of the reaction solution, for example.

Under the above reaction conditions, when a racemic tropic acid amide is used as a substrate, (R)-tropic acid and (S)-tropic acid amides can be obtained.

An optically active carboxylic acid and/or an optically active carboxylic acid amide generated by a reaction, such as an optically active tropic acid and an optically active tropic acid amide can be isolated and purified separately by a standard method. For example, a reaction solution containing an optically active tropic acid generated by a hydrolytic reaction is subjected to extraction with an organic solvent such as ethyl acetate or toluene, the organic solvent is distilled under reduced pressure, and then products of interest can be isolated and purified by treatment such as distillation, recrystallization or chromatography. Products of interest can also be isolated and purified by subjecting a filtrate obtained by removing microbial cells from the reaction solution to neutralization and crystallization using sulfuric acid or the like, and then filtering the precipitated product of interest.

EXAMPLES

The present invention is hereafter described in greater detail with reference to the following examples, although the present invention is not limited thereto. In addition, the symbol "%" as follows refers to "wt %" unless otherwise specified.

Reference Example 1

Synthesis of Racemic Tropic Acid Amide

Racemic tropic acid (49.85 g, 300 mmol) was agitated in methanol (250 ml) and concentrated sulfuric acid (0.5 g) at 80° C. for 20 hours, and then the solvent was distilled under reduced pressure. Thus, an oily methyl tropate product (9.3 g, 45.9 mmol) was obtained.

The above oily dimethyl tropate product (9.0 g, 44.5 mmol) was added to a pressure-tight container. After the addition of an aqueous ammonia solution (200 ml, 900 mmol), the solution was agitated in a closed system at room temperature for 20 hours, and the precipitated solid was obtained by filtration. The solid obtained by filtration was dried under reduced pressure, and thus a solid tropic acid amide (29 g, 176 mmol) was obtained.

Example 1

(1) Isolation and Purification of KNK AM38 Strain-Derived Amidase

A microorganism isolated from soil, the KNK AM38 strain, was inoculated into 60 ml of medium A sterilized within a test tube (glycerol (20 g), meat extract (10 g), yeast extract (5 g), polypeptone (10 g), and sodium chloride (3 g); diluted with deionized water to 1 L; pH 7.0 before sterilization) and then aerobically cultured with shaking at 30° C.

for 12 hours. The culture solution (15 ml) was inoculated to 3 L of medium A sterilized within a flask and then aerobically cultured with shaking at 30° C. for 24 hours. After the completion of culture, cells were collected by centrifugation, suspended in 100 mM phosphate buffer (pH 7.0), disrupted with ultrasonic waves, then centrifuged. Protamine sulfate was added to the supernatant at a final concentration of 0.5%, and the thus generated precipitate was removed by centrifugation. Glycerin was added to the supernatant solution at a final concentration of 10%. The solution was applied to DEAE-TOYOPEARL 650 M (TOSOH Corporation) to perform column chromatography. After washing with 20 mM phosphate buffer (pH7.0) containing 10% glycerin, elution was performed using the same buffer with a concentration gradient ranging from 0 M to 0.3 M sodium chloride, thereby collecting an active fraction. After ammonium sulfate was dissolved in the active fraction at a final concentration of 0.5 M, the solution was applied to Butyl-TOYOPEARL (TOSOH Corporation) to perform column chromatography. Elution was performed using 20 mM phosphate buffer (pH 7.0) containing 10% glycerin with a concentration gradient ranging from 0.5 M to 0 M ammonium sulfate. The thus obtained active fraction was dialyzed against 20 mM phosphate buffer (pH 7.0) containing 10% glycerin and then applied to Resource Q (Amersham Pharmacia Biotech) to perform column chromatography. After washing with 20 mM phosphate buffer (pH 7.0) containing 10% glycerin, elution was performed using the same buffer with a concentration gradient ranging from 0 M to 0.3 M sodium chloride. The thus obtained active fraction was applied to Superdex 200 HR 10/30 (Amersham Pharmacia Biotech) to perform gel filtration and then elution was performed with 20 mM phosphate buffer (pH 7.0) containing 10% glycerin and 0.15 M sodium chloride. The thus obtained active fraction was applied to Bio-Gel HT hydroxyapatite (Bio-Rad Laboratories, Inc.) to perform column chromatography. Elution was performed using phosphate buffer (pH 7.0) containing 10% glycerin with a concentration gradient ranging from 10 mM to 25 mM. The thus obtained active fraction was analyzed by SDS-polyacrylamide electrophoresis. As a result, amidase was detected as a single band and thus the purity of the purified enzyme could be confirmed.

(2) Cloning of Amidase Gene

First, cells obtained by culturing the KNK 38 strain by a method similar to that of (1) were lysed and treated using CTAB, chloroform, and phenol. The thus extracted DNA was precipitated with isopropanol. The precipitate obtained by centrifugation was washed with ethanol, and thus a chromosomal DNA was prepared. Subsequently, the amino terminal amino acid sequence of the amidase purified in (1) was determined using a gas phase protein sequencer. Furthermore, a polypeptide fragment generated by causing V8 protease to act on the amidase purified in (1) in the presence of 4 M urea was purified using reverse phase HPLC, and then the internal amino acid sequence of amidase was determined by a method similar to the above. PCR was performed using a DNA primer (Primer-1: SEQ ID NO: 9) designed based on the N-terminal amino acid sequence, a DNA primer (Primer-2: SEQ ID NO: 10) designed based on the internal amino acid sequence, and the previously obtained chromosomal DNA as a template. As a result, a portion (referred to as "partial gene") of the amidase gene of interest was obtained.

Next, the following procedure was performed to obtain the full-length gene of interest. DNA primers (Primer-3: SEQ ID NO: 11, and, Primer-4: SEQ ID NO: 12) directed toward outside of the partial gene were synthesized based on the nucleotide sequences that correspond to the respective N-terminal and C-terminal portions of the amidase enzyme. Inverse PCR was performed using the above primers and a template DNA prepared by digesting the previously obtained chromosomal DNA with restriction enzymes, Apa I, ApaL I, and BspT104 I to produce fragments, followed by ligation and cyclization of the fragments with T4 DNA ligase.

Therefore, a DNA fragment containing gene portions located outside the previously obtained partial gene was obtained. After determination of the nucleotide sequence of the DNA fragment, a DNA primer (Primer-5: SEQ ID NO: 13) comprising a sequence prepared by ligating the cleavage site of restriction enzyme EcoR I to the nucleotide sequence of a portion assumed to be located upstream of the N-terminus of the enzyme, and a DNA primer (Primer-6: SEQ ID NO: 14) comprising a sequence prepared by ligating the cleavage site of restriction enzyme Sac I to the nucleotide sequence of a portion assumed to be located downstream of the C-terminus were prepared. The DNA between the sequences was amplified by PCR using these DNA primers, and thus a DNA fragment containing the full-length amidase gene was obtained. A partial nucleotide sequence of the thus obtained DNA fragment was analyzed, thereby confirming that the full-length amidase gene (SEQ ID NO: 2) was contained.

(3) Cloning of Amidase Gene from KNK AM40 Strain, KNK AM1011 Strain, and KNK AM250 Strain PCR was performed using DNA primers (Primer-7: SEQ ID NO: 15 and Primer-8: SEQ ID NO: 16) designed based on the nucleotide sequence shown in SEQ ID NO: 2 in (1) and a known nucleotide sequence having high homology with SEQ ID NO: 2, and using as templates the chromosomal DNAs of the KNK AM40 strain, the KNK AM1011 strain, and the KNK AM250 strain obtained by the method described in (1). As a result, a portion of the amidase gene of interest were obtained. Procedures similar to the method described in (2) for obtaining the full-length gene of interest were performed. Thus DNAs comprising the nucleotide sequences shown in SEQ ID NOS: 4, 6, and 8 were obtained.

Example 2

Preparation of Amidase

The DNA fragments obtained in Example 1 from the KNK AM38 strain, the KNK AM1011 strain, and the KNK AM250 strain were each inserted between an EcoR I recognition site and a Sac I recognition site downstream of a lac promoter of plasmid pUCN18, which is constructed via PCR by modifying the $185^{th}$ T to A of pUC18 (Takara Bio Inc., GenBank Accession No. L09136) to disrupt the Nde I site, and further modifying the $471^{st}$ to $472^{nd}$ GC to TG of the same to introduce a new Nde I site, thereby constructing recombinant vectors pNAM38, pNAM1011, and pNAM250. Moreover, the KNK AM40 strain-derived DNA fragment obtained in Example 1 was inserted between an EcoR I recognition site and a Sph I recognition site downstream of the lac promoter of plasmid pUCN18, thereby constructing a recombinant vector, pNAM40. *E. coli* HB101 competent cells (Takara Bio Inc.) were transformed with these recombinant vectors pNAM38, pNAM40, pNAM1011, and pNAM250, thereby obtaining *E. coli* HB101 (pNAM38), *E. coli* HB101 (pNAM40), *E. coli* HB101 (pNAM1011), and *E. coli* HB101 (pNAM250). The thus obtained transformants were inoculated in 5 ml of 2×YT medium (triptone 1.6%, yeast extract 1.0%, NaCl 0.5%, pH 7.0) containing 200 μg/ml ampicillin, followed by 24 hours of shaking culture at 37° C. Cells were collected by centrifugation, and then suspended in 5 ml of 100 mM phosphate buffer (pH 7.0).

Example 3

R-selective Hydrolysis of Racemic Tropic Acid Amide 1 ml of the cell suspension prepared in Example 2 was mixed with 20 mg of a tropic acid amide as a substrate synthesized by the method described in Reference example 1, and then the mixture was shaken at 30° C. for 24 hours. After the completion of the reaction, the solid matter was removed by centrifugation, and then the substrate and the product in the reaction solution were analyzed by high-performance liquid chromatography. Thus, conversion rate (%) was found by the following formula. Furthermore, the reaction solution was adjusted with 1 N hydrochloric acid to pH 2, tropic acid obtained by extraction with ethyl acetate was analyzed by high-performance liquid chromatography, and thus optical purity (% ee) was found by the following formula.

Conversion rate (%)=amount of product/(amount of substrate+amount of product)×100

Optical purity (% $ee$)=($A$−$B$)/($A$+$B$)×100 ($A$ and $B$ represent the amounts of the corresponding enantiomers, $A$>$B$)

Conditions for the above high-performance liquid chromatography are as follows.
[Analysis of Conversion Rate]
Column: 5C18-ARII (4.6 mmϕ×250 mm, NACALAI TESQUE, INC.)
Eluent: 20 mM aqueous phosphoric acid solution (pH 2.5)/acetonitrile=6/4
Flow rate: 0.5 ml/minute
Column temperature: 30° C.
Measured wavelength: 210 nm
[Analysis of Optical Purity]
Column: CHIRALCEL OD-H (4.6 mmϕ×250 mm, Daicel Corporation)
Eluent: hexane/isopropyl alcohol/trifluoroacetic acid=95/5/0.1
Flow rate: 0.7 ml/minute
Column temperature: 35° C.
Measured wavelength: 254 nm The thus obtained results are shown in Table 1.

TABLE 1

| Enzyme-derived microorganism | Conversion rate (%) | Optical purity (% ee) | Absolute configuration |
|---|---|---|---|
| *E. coli* HB101 (pNAM38) | 48.6 | 96.4 | R |
| *E. coli* HB101 (pNAM40) | 49.8 | 96.2 | R |
| *E. coli* HB101 (pNAM1011) | 34.9 | 97.3 | R |
| *E. coli* HB101 (pNAM250) | 48.5 | 95.4 | R |

INDUSTRIAL APPLICABILITY

The present invention can be applied to the field of production of an optically active carboxylic acid and/or an optically active amide serving as a synthetic raw material or an intermediate for pharmaceutical products, for example.

All publications, patents, and patent applications cited herein are incorporated herein by reference in their entirety.

The invention claimed is:

1. A vector containing a DNA encoding a polypeptide having activity to selectively hydrolyze a (R)-tropic acid amide in a racemic mixture, wherein said polypeptide is selected from the group consisting of:
   (a) a polypeptide consisting of the amino acid sequence of SEQ ID NO: 1, 3, 5 or 7;
   (b) a polypeptide consisting of an amino acid sequence that has a deletion, an insertion, a substitution and/or an addition of 30 or less amino acids with respect to the amino acid sequence of SEQ ID NO: 1, 3, 5 or 7; and
   (c) a polypeptide consisting of an amino acid sequence that has 95% or more sequence identity with the amino acid sequence of SEQ ID NO: 1, 3, 5, or 7.

2. A transformant which is obtained by the transformation of a host cell with the vector according to claim 1.

3. The transformant according to claim 2, wherein the host cell is *Escherichia coli*.

4. A method for producing a polypeptide having activity to selectively hydrolyze a (R)-tropic acid amide in a racemic mixture, wherein said polypeptide is selected from the group consisting of:
   (a) a polypeptide consisting of the amino acid sequence of SEQ ID NO: 1, 3, 5 or 7;
   (b) a polypeptide consisting of an amino acid sequence that has a deletion, an insertion, a substitution and/or an addition of 30 or less amino acids with respect to the amino acid sequence of SEQ ID NO: 1, 3, 5 or 7; and
   (c) a polypeptide consisting of an amino acid sequence that has 95% or more sequence identity with the amino acid sequence of SEQ ID NO: 1, 3, 5, or 7, said method comprising culturing the transformant according to claim 2 or 3 in a medium, and collecting at least one of the expressed polypeptides of (a) to (c) from the culture.

5. The vector according to claim 1, wherein the polypeptide of (b) consists of an amino acid sequence that has a deletion, an insertion, a substitution and/or an addition of 10 or less amino acids with respect to the amino acid sequence of SEQ ID NO: 1, 3, 5 or 7.

6. The method for producing the polypeptide according to claim 4, wherein the polypeptide of (b) consists of an amino acid sequence that has a deletion, an insertion, a substitution and/or an addition of 10 or less amino acids with respect to the amino acid sequence of SEQ ID NO: 1, 3, 5 or 7.

* * * * *